United States Patent
Aram et al.

(10) Patent No.: US 8,403,993 B2
(45) Date of Patent: Mar. 26, 2013

(54) MODULAR FIXED AND MOBILE BEARING PROSTHESIS SYSTEM

(75) Inventors: Luke J. Aram, Warsaw, IN (US); Adam I. Hayden, Fort Wayne, IN (US)

(73) Assignee: DePuy Products, Inc., Warsaw, IN (US)

( * ) Notice: Subject to any disclaimer, the term of this patent is extended or adjusted under 35 U.S.C. 154(b) by 1259 days.

(21) Appl. No.: 11/554,631

(22) Filed: Oct. 31, 2006

(65) Prior Publication Data
US 2007/0100463 A1 May 3, 2007

Related U.S. Application Data

(60) Provisional application No. 60/732,000, filed on Oct. 31, 2005.

(51) Int. Cl.
*A61F 2/38* (2006.01)
(52) U.S. Cl. ............. 623/20.33; 623/20.29; 623/20.28
(58) Field of Classification Search .... 623/20.14–20.15, 623/20.21, 20.27–20.29, 20.31–20.36
See application file for complete search history.

(56) References Cited

U.S. PATENT DOCUMENTS

| | | | |
|---|---|---|---|
| 4,205,400 A | 6/1980 | Shen et al. | |
| 4,217,666 A | 8/1980 | Averill | |
| 4,501,031 A | 2/1985 | McDaniel et al. | |
| 4,822,366 A | 4/1989 | Bolesky | |
| 4,944,757 A | 7/1990 | Martinez et al. | |
| 5,108,442 A | 4/1992 | Smith | |
| 5,326,358 A | 7/1994 | Aubriot et al. | |
| 5,326,359 A | 7/1994 | Oudard | |
| 5,370,699 A | 12/1994 | Hood et al. | |
| 5,489,311 A | 2/1996 | Cipolletti | |
| 5,782,925 A | 7/1998 | Collazo et al. | |
| 5,871,545 A | 2/1999 | Goodfellow et al. | |
| 5,879,391 A | 3/1999 | Slamin | |
| 5,879,392 A | 3/1999 | McMinn | |
| 5,951,603 A | 9/1999 | O'Neil et al. | |
| 6,010,534 A | 1/2000 | O'Neil et al. | |
| 6,013,103 A | 1/2000 | Kaufman et al. | |
| 6,033,440 A | 3/2000 | Schall et al. | |
| 6,053,945 A * | 4/2000 | O'Neil et al. | 623/20.32 |
| 6,090,144 A | 7/2000 | Letot et al. | |
| 6,162,254 A | 12/2000 | Timoteo | |
| 6,210,444 B1 | 4/2001 | Webster et al. | |
| 6,306,172 B1 | 10/2001 | O'Neil et al. | |

(Continued)

FOREIGN PATENT DOCUMENTS

EP 0 682 925 A1 6/1992
EP 0 904 748 A2 9/1998

(Continued)

OTHER PUBLICATIONS

Australian Search Report From Corresponding Application No. 2006308865, Dated Feb. 6, 2012, 2 Pages.

(Continued)

*Primary Examiner* — Thomas J Sweet
*Assistant Examiner* — Rebecca Preston

(57) ABSTRACT

A knee prosthetic system includes a femoral component, a fixed tibial bearing component, a mobile tibial bearing component and an integrated or common tibial base component. The same tibial base component can be used with either the fixed tibial bearing component or the mobile tibial bearing component. The fixed bearing component and tibial base component have mating anti-rotation features. One embodiment of the mobile bearing component does not engage the anti-rotation feature of the tibial base component. Another embodiment engages the anti-rotation feature to allow for limited rotation.

6 Claims, 6 Drawing Sheets

U.S. PATENT DOCUMENTS

| | | | |
|---|---|---|---|
| 6,391,283 | B1 | 5/2002 | Jensen et al. |
| 6,506,215 | B1 | 1/2003 | Letot et al. |
| 6,506,216 | B1 | 1/2003 | McCue et al. |
| 6,540,787 | B2 | 4/2003 | Biegun et al. |
| 6,558,427 | B2 | 5/2003 | Leclercq et al. |
| 6,610,097 | B2 | 8/2003 | Serbousek et al. |
| 6,623,526 | B1 | 9/2003 | Lloyd |
| 6,660,039 | B1 | 12/2003 | Evans et al. |
| 6,709,462 | B2 | 3/2004 | Hanssen |
| 6,755,864 | B1 * | 6/2004 | Brack et al. ............... 623/20.29 |
| 6,916,340 | B2 | 7/2005 | Metzger et al. |
| 7,740,662 | B2 | 6/2010 | Barnett et al. |
| 7,883,653 | B2 | 2/2011 | Smith et al. |
| 2001/0014827 | A1 | 8/2001 | Chambat et al. |
| 2001/0021877 | A1 | 9/2001 | Biegun et al. |
| 2002/0072802 | A1 * | 6/2002 | O'Neil et al. ............. 623/20.33 |
| 2002/0120341 | A1 | 8/2002 | Stumpo et al. |
| 2003/0009232 | A1 | 1/2003 | Metzger et al. |
| 2003/0153980 | A1 | 8/2003 | Brack |
| 2003/0195634 | A1 | 10/2003 | Fenning et al. |
| 2003/0204264 | A1 | 10/2003 | Stumpo et al. |
| 2004/0034432 | A1 | 2/2004 | Hughes et al. |
| 2004/0143337 | A1 | 7/2004 | Burkinshaw |
| 2004/0186583 | A1 | 9/2004 | Keller |
| 2004/0204765 | A1 | 10/2004 | Fenning et al. |
| 2004/0215345 | A1 | 10/2004 | Perrone et al. |
| 2004/0225368 | A1 | 11/2004 | Plumet et al. |
| 2004/0236428 | A1 | 11/2004 | Burkinshaw et al. |
| 2004/0267371 | A1 | 12/2004 | Hayes, Jr. et al. |
| 2005/0027365 | A1 | 2/2005 | Burstein et al. |
| 2005/0222686 | A1 | 10/2005 | Brehm |
| 2005/0246027 | A1 | 11/2005 | Metzger et al. |
| 2005/0283250 | A1 | 12/2005 | Coon et al. |
| 2006/0155383 | A1 | 7/2006 | Smith et al. |
| 2007/0100463 | A1 | 5/2007 | Aram et al. |
| 2008/0051908 | A1 | 2/2008 | Angibaud et al. |
| 2008/0091271 | A1 | 4/2008 | Bonitati et al. |
| 2008/0091272 | A1 | 4/2008 | Aram et al. |
| 2008/0091273 | A1 | 4/2008 | Hazebrouck |
| 2008/0097616 | A1 | 4/2008 | Meyers et al. |
| 2008/0114463 | A1 | 5/2008 | Auger et al. |
| 2008/0114464 | A1 | 5/2008 | Barnett et al. |
| 2010/0222890 | A1 | 9/2010 | Barnett et al. |

FOREIGN PATENT DOCUMENTS

| | | |
|---|---|---|
| EP | 0 904 749 A2 | 9/1998 |
| EP | 0 925 765 A2 | 12/1998 |
| EP | 0 956 836 A1 | 5/1999 |
| EP | 1 025 818 A2 | 2/2000 |
| EP | 1 129 676 A1 | 2/2001 |
| EP | 1 702 590 A2 | 2/2006 |
| WO | 79/00739 A1 | 10/1979 |
| WO | 03/065939 A1 | 8/2003 |

OTHER PUBLICATIONS

Australian Search Report From Corresponding Application No. 2006308865, Dated Nov. 15, 2011, 4 Pages.

Chinese Search Report (First Office Action) From Corresponding Application No. 200680049871.6, Dated Apr. 14, 2010, 7 Pages.

European Search Report From Corresponding Application No. 06827110.5-1526/1945151, Dated Aug. 10, 2009, 3 Pages.

Japanese Search Report From Corresponding Application No. 2008-538091, Dated May 31, 2011, 3 Pages.

Patent Cooperation Treaty Search Report From Corresponding Application No. PCT/7506/42366, Dated Aug. 8, 2007, 4 Pages.

* cited by examiner

MODULAR FIXED AND MOBILE BEARING PROSTHESIS SYSTEM

CROSS-REFERENCE TO RELATED APPLICATIONS

Priority is claimed to the following application: U.S. Provisional Patent Application Ser. No. 60/732,000 entitled, "MODULAR FIXED AND MOBILE BEARING PROSTHESIS SYSTEM," filed on Oct. 31, 2005 by Adam I. Hayden and Luke J. Aram.

FIELD OF THE INVENTION

This invention relates generally to prostheses for human body joints, and more particularly, to prostheses for human knees.

BACKGROUND OF THE INVENTION

When a human skeletal joint is damaged, whether as a result of an accident or illness, a prosthetic replacement of the damaged joint may be necessary to relieve pain and to restore normal use to the joint. Typically the entire joint is replaced by means of a surgical procedure that involves removal of the ends of the corresponding damaged bones and replacement of these ends with prosthetic implants. This replacement of a native joint with a prosthetic joint is referred to as a primary total-joint arthroplasty.

For a damaged human knee, the total knee is commonly replaced with prosthetic components shaped to replace portions of the distal femur, proximal tibia and patella. Prosthetic components for use in replacing the distal femur are shaped to replace the articulating surfaces of the medial condyle, lateral condyle and trochlea, and prosthetic components for use in replacing the proximal tibia are shaped to replace the tibial plateau. Commonly, the tibial component is two-piece: a tibial tray is affixed to the bone and a bearing is received on the tibial tray. The tray is commonly made of metal, such as a cobalt-chrome alloy or titanium alloy, and the bearing is commonly made of a polymer material such as ultrahigh molecular weight polyethylene.

Several alternative designs for total knee prostheses have been available in the past. Some knee prostheses are designed for use when the cruciate ligaments are retained; some are designed for use when the cruciate ligaments are removed. Some of these alternative knee prostheses can be distinguished by the type of tibial components used: some designs provide a fixed bearing, wherein the position of the bearing component is locked with respect to the tibial tray; other designs allow for movement of the bearing with respect to the tibial tray. The designs that allow for movement of the bearing component with respect to the tibial tray are commonly referred to as mobile bearing designs or rotating platform designs.

In fixed bearing designs, the tibial trays commonly have sidewalls, projections, flanges or dovetails that mate with features on the bearing component to lock the tibial tray and bearing component together. In contrast, in rotating platform or mobile bearing designs, the superior or proximal surface of the tibial tray typically does not include such sidewalls or surface features; instead, the proximal surface of the tray is usually planar and smooth, to enable the bearing insert to rotate. In typical fixed bearing designs where the bearing and the base are locked around their peripheries, the size of the bearing component is dictated by the size and features of the tibial base component, so that the bearing component is properly fixed in position on the base; accordingly, the match between the femoral component and the bearing component may not be ideal. In mobile bearing designs, since the bearing component does not need to mate with any locking mechanism around the periphery of the bearing or base, the surgeon has greater flexibility in ensuring an ideal match between the bearing component and the femoral component.

The decision as to whether to use a fixed bearing design or mobile bearing design is based on a number of factors, including surgeon preference and the needs of the individual patient. For example, use of a mobile bearing design may provide the patient with a more natural feel to the joint. However, if the soft tissue of the knee joint is in poor condition (e.g. the collateral ligaments are compromised), it may be advisable to use a fixed bearing design to provide the patient with greater stability. Sometimes, the decision as to whether to use a fixed or mobile bearing design is not made until the condition of the patient's soft tissue can be evaluated intraoperatively.

On occasion, the primary prosthesis fails. Failure can result from many causes, including wear, aseptic loosening, osteolysis, ligamentous instability, arthrofibrosis and patellofemoral complications. When the failure is debilitating, revision surgery may be necessary. In a revision, the primary prosthesis is typically removed and replaced with components of a revision prosthetic system.

In the case of a primary knee prosthesis utilizing a mobile bearing design, the revision procedure may involve changing the prosthesis to a fixed bearing design. This change can result from several factors, such as deterioration of the knee ligaments. Because the features of the tibial base components of fixed and mobile bearing designs are vastly different, revision from a mobile bearing design to a fixed bearing design with existing implant systems typically requires removal of the tibial base component and replacement with a tibial base component that is appropriate for a fixed bearing configuration.

Accordingly, there is a need for a prosthetic knee system that allows the surgeon to choose intraoperatively whether to use a fixed bearing or mobile bearing implant system. In addition, there is a need for such a system that allows the surgeon to focus on providing the optimum match between the tibial insert and the femoral component in a fixed bearing option, rather than being required to select a particular tibial insert bearing size to match the tibial tray. Moreover, there is a need for a prosthetic knee system that allows for a change from a mobile bearing design to a fixed bearing design without removing the tibial base component from the tibia. Conversely, there is a need for a system that allows for conversion from a fixed to a mobile bearing design. This may occur if a surgeon observes a great deal of joint space narrowing on an x-ray or during a revision surgery. In this situation, the surgeon may decide to replace the fixed bearing insert with a lower wearing mobile bearing insert.

Prior art systems providing designs for forming either a fixed or a mobile bearing include U.S. Pat. No. 6,709,462 entitled "Modular Joint Prosthesis System," and U.S. Pat. Publication No. U.S.20040215345A1 entitled "Rotating/Non-Rotating Tibia Base Plate/Insert System."

SUMMARY OF THE INVENTION

In one aspect, the present invention provides a prosthetic knee system comprising a femoral component, a tibial base component, a first tibial bearing component and a second tibial bearing component. The femoral component has bearing surfaces. The tibial base component includes a tray and a stem. The tray has a flat proximal surface and a distal surface.

The stem extends distally from the distal surface of the tray. The stem has a longitudinal axis and a distal end spaced from the tray. The tibial base component has a longitudinal bore contained within the stem. The longitudinal bore extends from the stem through the tray and through the proximal surface of the tray. The longitudinal bore is circular in transverse cross-section along a portion of the axial length of the longitudinal bore within the stem. The first tibial bearing component has a proximal bearing surface, a flat distal surface and a stem extending distally from the flat distal surface. The stem of the first bearing component has a longitudinal axis and a distal end spaced from the flat distal surface. The second tibial bearing component has a proximal bearing surface, a distal surface and a stem extending distally from the flat distal surface. The stem of the second tibial bearing component has a longitudinal axis and a distal end spaced from the distal surface. The first tibial bearing component and second tibial bearing component are both sized and shaped so as to be capable of being selectively assembled with the tibial base component with the stem of the bearing component received in the longitudinal bore. The tibial base component and one of the tibial bearing components include mating anti-rotation features to fix the rotational position of the tibial bearing component with respect to the tibial base component when assembled; the other tibial bearing component is shaped so as to be rotatable about the longitudinal axis of the stem when assembled with the tibial base component.

In another aspect, the present invention provides a prosthetic knee system comprising a femoral component, a tibial base component, a first tibial bearing component and a second tibial bearing component. The femoral component has bearing surfaces. The tibial base component comprises a tray and a stem. The tray has a planar proximal surface and a distal surface. The stem extends distally from the distal surface of the tray, and has a longitudinal axis, a distal end spaced from the tray and an interior surface defining a longitudinal bore contained within the stem. The interior surface extends distally from the proximal surface of the tray into the stem. The longitudinal bore extends from the stem through the tray and through the proximal surface of the tray. The longitudinal bore is non-circular in transverse cross-section along a portion of its axial length and is circular in transverse cross-section along the remainder of its axial length. The first tibial bearing component has a proximal bearing surface, a flat distal surface and a stem extending distally from the flat distal surface. The stem has a longitudinal axis and a distal end spaced from the flat distal surface. The stem of the first tibial bearing component is non-circular in transverse cross-section along at least a portion of its axial length. The second tibial bearing component has a proximal bearing surface, a distal surface and a stem extending distally from the flat distal surface. The stem has a longitudinal axis and a distal end spaced from the distal surface. The stem of the second tibial bearing component is circular in transverse cross-section along the entire axial length of the stem. Each tibial bearing component is capable of being selectively assembled with the tibial base component with the stem of the tibial bearing component received in the longitudinal bore of the tibial base component. The portion of the longitudinal bore with a non-circular transverse cross-section and the portion of the stem of the first tibial bearing component with a non-circular transverse cross-section have mating shapes to fix the rotational position of the first tibial bearing component with respect to the tibial base component when the stem of the first tibial bearing component is received in the longitudinal bore of the tibial base component. The longitudinal bore of the tibial base component and the stem of the second tibial bearing component are sized and shaped so that the second tibial bearing component can rotate about the longitudinal axis of the stem when the stem of the second tibial bearing component is received in the longitudinal bore of the stem of the tibial base component.

In another aspect, the present invention provides a tibial base component for use in knee arthroplasty. The tibial base component comprises a tray and a stem. The tray has a flat proximal surface and a distal surface. The stem extends distally from the distal surface of the tray. The stem has a longitudinal axis and a distal end spaced from the tray. The tibial base component also has an interior surface extending distally from the proximal surface of the tray into the stem. The interior surface defines a longitudinal bore contained within the stem. The longitudinal bore is circular in transverse cross-section along a portion of the axial length of the longitudinal bore. The interior surface has a radial recess and a radial stop positioned distal to the proximal surface of the tray.

In another aspect, the present invention provides a tibial base component for use in knee arthroplasty comprising a tray and a stem. The tray has a flat proximal surface and a distal surface. The stem extends distally from the distal surface of the tray, and has a longitudinal axis and a distal end spaced from the tray. The tibial base component also has an interior surface defining a longitudinal bore contained within the stem. The longitudinal bore extends from the stem to the proximal surface of the tray. The longitudinal bore is circular in transverse cross-section along a portion of the axial length of the longitudinal bore and non-circular in transverse cross-section along a portion of the axial length of the longitudinal bore.

In another aspect, the present invention provides a tibial bearing component with a proximal bearing surface, a flat distal surface and an integral stem extending distally from the distal surface. The stem includes an outer surface, a longitudinal axis, a distal end, a portion that is circular in transverse cross-section, and a protrusion extending outward from the outer surface of the stem and distally from the distal surface. The stem has a maximum transverse dimension at the protrusion and a minimum transverse dimension at the distal end of the stem.

In another aspect, the present invention provides a tibial bearing component comprising a proximal bearing surface, a flat distal surface, and an integral stem extending distally from the distal surface. The stem has an outer surface and a longitudinal axis. A portion of the outer surface of the stem has a non-circular transverse cross-section and a portion of the outer surface of the stem has a circular transverse cross-section.

DETAILED DESCRIPTION

Figure 1:
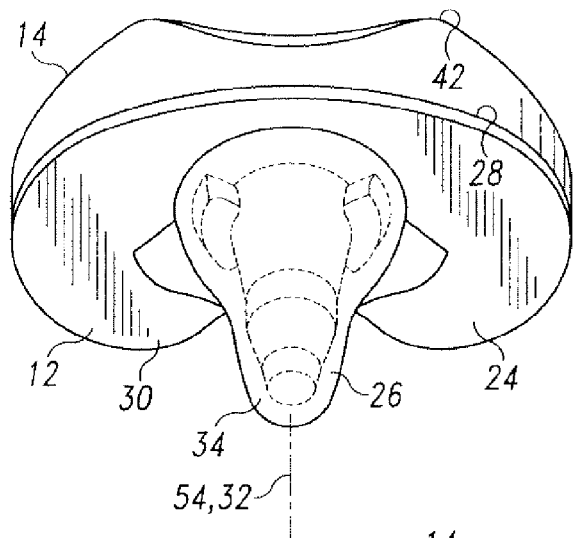
FIG. 1 is a perspective view of an assembly of a tibial base component and a tibial bearing component.
Figure 2:
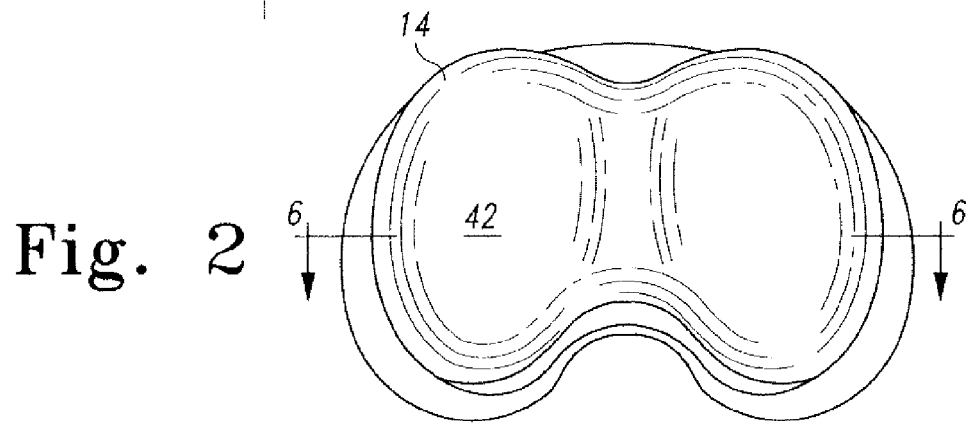
FIG. 2 is a top plan view of the assembly of FIG. 1.

The present invention provides a prosthetic knee system that includes a femoral implant component 10 (illustrated in FIG. 13), a common tibial base component 12 (illustrated in FIGS. 1-3, 5-8 and 10-12), and interchangeable bearing components 14, 16 that can each be selectively assembled with the common tibial base component 12. The first bearing a component 14 is a fixed bearing component; the second bearing component 16 is a mobile bearing component.

Figure 13:
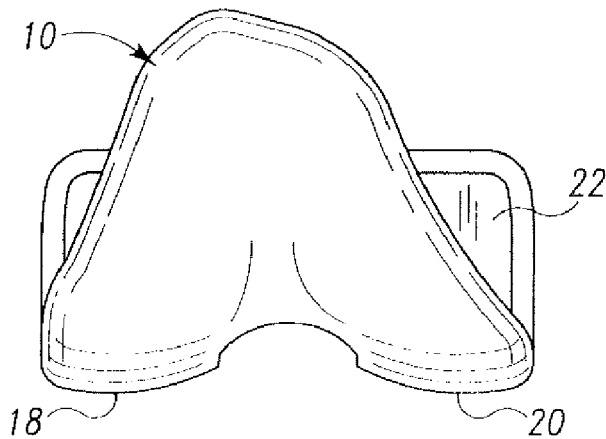
FIG. 13 is a front elevation of a femoral implant component that may be used with the prosthetic knee system of the present invention.

The femoral component 10 of FIG. 13 includes two convex bearing surfaces 18, 20. The femoral component 10 may be made of standard materials such as a cobalt-chrome alloy or a titanium alloy and may include standard features for such femoral implants. For example, the bone-facing portion 22 may be porous for bone ingrowth or may have recesses to enhance cemented fixation. The invention is not limited to any particular type of femoral component or to any particular feature unless expressly called for in the claims.

Figure 3:
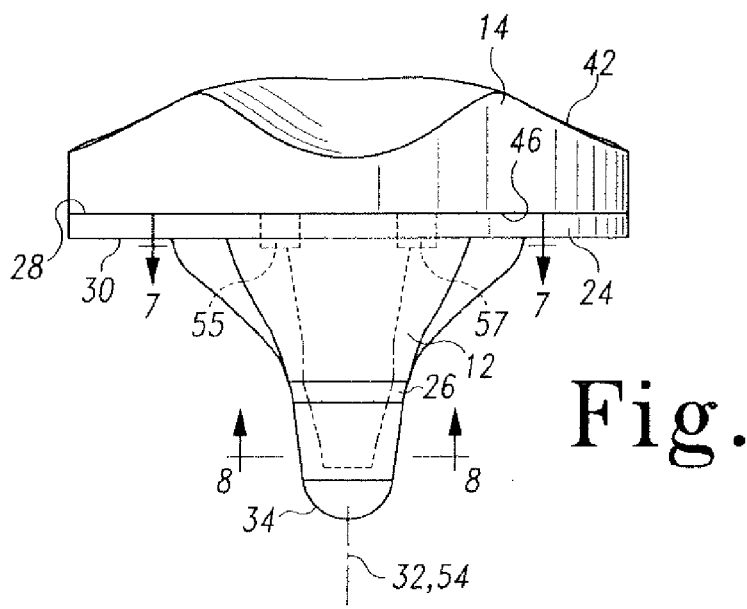
FIG. 3 is a front elevation of the assembly of FIGS. 1-2.
Figure 5:
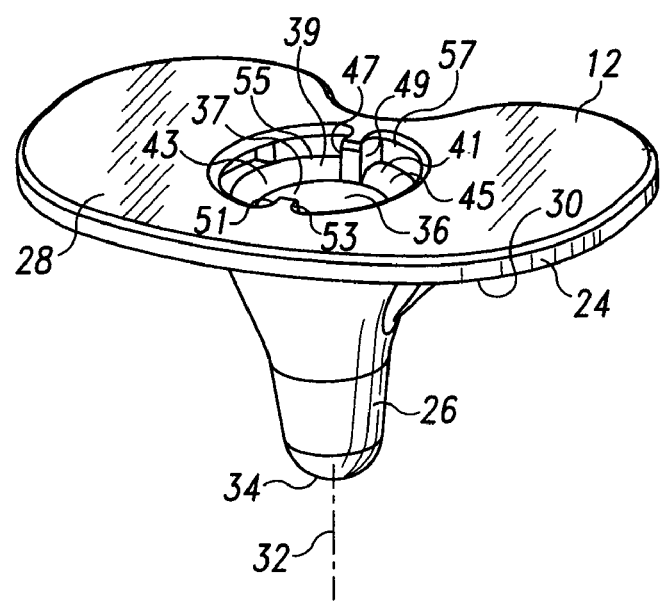
FIG. 5 is a perspective view of the tibial base component of FIGS. 1-3.

As illustrated in FIGS. 1, 3 and 5, the tibial base component 12 comprises a tray 24 and an integral stem 26. The tray 24 has a flat or planar proximal or superior surface 28 and a distal or inferior surface 30. For optimum performance as part of a mobile bearing system, the planar proximal or superior surface 28 of the tray 24 may be highly polished. The stem 26 extends distally from the distal surface 30 of the tray 24. The stem 26 has a central longitudinal axis 32 and a distal end 34 spaced from the tray 24.

As shown in FIG. 5, the tibial base component 12 also has a longitudinal bore 36 that extends along the central longitudinal axis 32 of the stem 26, through the tray 24 and through the proximal surface 28 of the tray 24. The longitudinal bore 36 is defined by an interior surface 37 that is continuous with the superior or proximal surface 28 of the tray 24. The interior surface 37 extends distally from the proximal surface 28 of the tray 24 into the stem 26.

Figure 6:
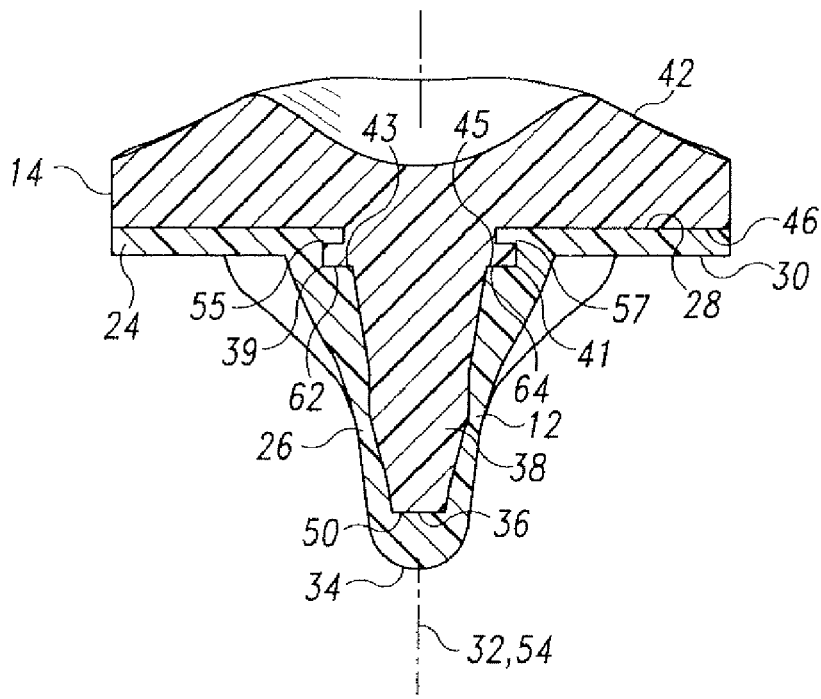
FIG. 6 is a cross-section of the assembly of FIGS. 1-3, taken along line 6-6 of FIG. 2.
Figure 10:
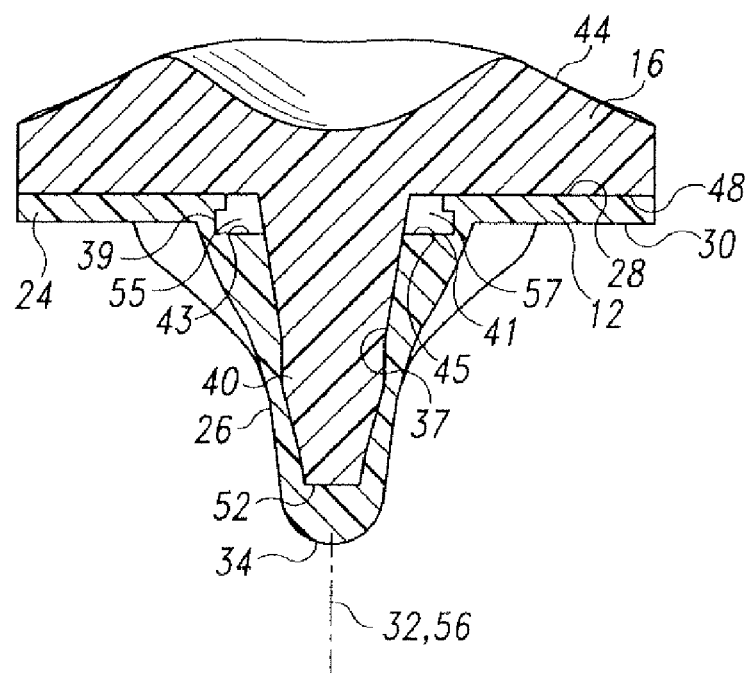
FIG. 10 is a cross-section similar to FIG. 6, but illustrating the tibial bearing component of FIG. 9 assembled with the tibial base component.
Figure 11:
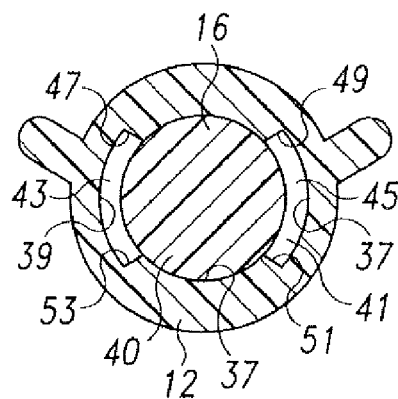
FIG. 11 is a transverse cross-section similar to FIG. 7, but illustrating the tibial bearing component of FIG. 9 assembled with the tibial base component.
Figure 12:
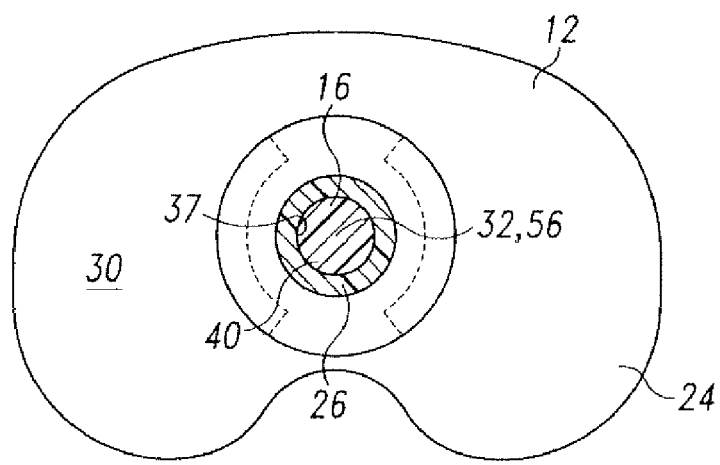
FIG. 12 is a transverse cross-section similar to FIG. 8, but illustrating the tibial bearing component of FIG. 9 assembled with the tibial base component.

As shown in FIGS. 5-6 and 10, the interior surface 37 of the tibial base component 12 defines two radial recesses 39, 41 at the proximal end of the longitudinal bore 36. The radial recesses 39, 41 comprise radial surfaces 43, 45 that lie in a common plane that is perpendicular to the central longitudinal axis 32 of the stem 26. As shown in FIG. 5, the interior surface 37 of the tibial base component also defines four spaced stop surfaces 47, 49, 51, 53. The stop surfaces 47, 49, 51, 53 are generally flat and are perpendicular to the radial surfaces 43, 45. The stop surfaces 47, 49, 51, 53 are oriented in longitudinal planes that are generally radially aligned in the illustrated embodiment. The radial surfaces 43, 45 and stop surfaces 47, 49, 51, 53 are all positioned below the level of the superior or proximal surface 28 of the tibial base component 12, and in the illustrated embodiment extend below the level of the distal or inferior surface 30.

In the illustrated embodiment, the distal end 34 of the stem 26 is closed and the longitudinal bore 36 defines a blind bore. It should be understood that the distal end 34 of the stem 26 could have features that would allow a stem extension (not shown) to be attached to the tibial base component, in which case the longitudinal bore 36 may extend through the entire length of the stem 26. In the illustrated embodiments, the interior surface 37 defining the longitudinal bore 36 tapers in a distal direction between the radial surfaces 43, 45 and the distal end 34 of the tibial base component 12.

A substantial part of the longitudinal bore 36 of the tibial base component 12 receives a substantial part of an elongated stem 38, 40 of the either of the bearing components 14, 16. The two bearing components 14, 16 share several common features. Both bearing components 14, 16 have a proximal or superior bearing surface 42, 44. These bearing surfaces 42, 44 include concave areas shaped to receive the bearing surfaces 18, 20 of the femoral component 10. Both bearing components 14, 16 also have distal or inferior surfaces 46, 48; these distal surfaces 46, 48 are flat or planar, to be received on the planar superior or proximal surface 28 of the tibial base component 12. The stems 38, 40 of both bearing components 14, 16 extend distally from the distal or inferior surfaces 46, 48 to distal ends 50, 52 that are spaced from the distal or inferior surfaces 46, 48. The stems 38, 40 have central longitudinal axes 54, 56.

Each of the bearing components 14, 16 is sized and shaped so as to be capable of being selectively assembled with the tibial base component 12. The stems 38, 40 of the bearing components are generally sized and shaped so that they can be received in the longitudinal bore 36 in the stem 26 of the tibial base component 12. FIGS. 6 and 10 illustrate the stems 38, 40 of the bearing components 14, 16 received in the longitudinal bore 36 of the base component 12. Generally, there is a relatively tight fit between the bearing stems 38, 40 and the interior surface 37 of the base component 12 for stability, although the fit of at least one of the bearing components 16 allows for rotation of the stem 40 about its central longitudinal axis 56. The outer surfaces of parts of the stems 38, 40 are tapered to match the taper of the longitudinal bore 36. The distal or inferior surfaces 46, 48 of the bearing components 14, 16 are planar to match the planar proximal or superior surface 28 of the base component 12. The tibial base 12 and fixed bearing 14 may also have mating features that prevent the bearing 14 from lifting off of the tibial base 12. In the illustrated embodiment, the tibial base has a pair of undercuts 55, 57 and the fixed bearing protrusions 58, 60 are shaped to fit within the undercuts. It should be understood that these anti-lift features are provided as examples only; other anti-lift features may be used in the present invention.

Figure 4:
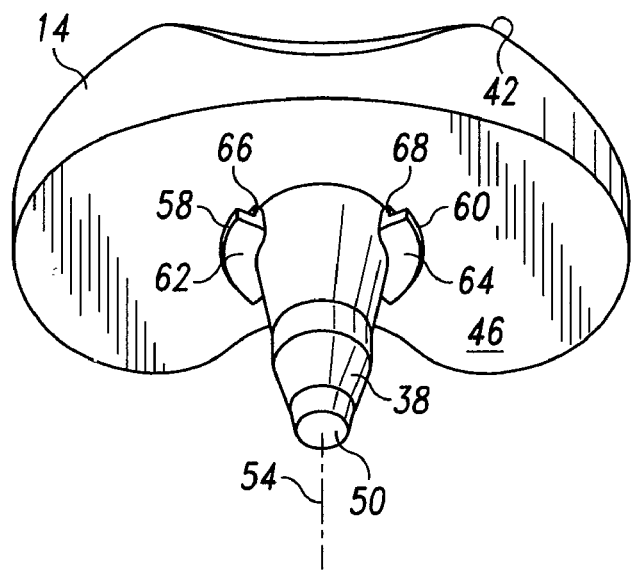
FIG. 4 is a perspective view of one of the tibial bearing components that can be assembled with the tibial base component of FIGS. 1 and 3.
Figure 7:
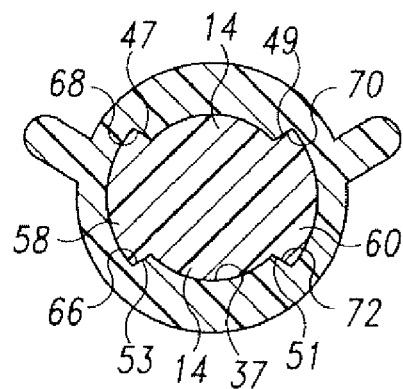
FIG. 7 is a transverse cross-section of the assembly of FIGS. 1-3, taken along line 7-7 of FIG. 3.
Figure 8:
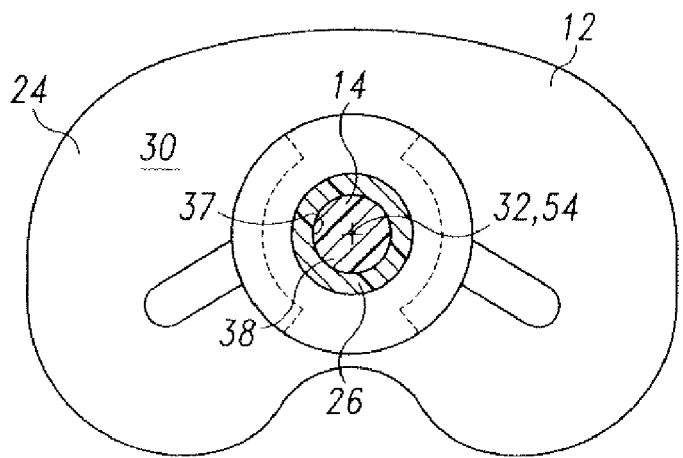
FIG. 8 is a transverse cross-section of the assembly of FIGS. 1-3, taken along line 8-8 of FIG. 3.

The fixed bearing component 14 and mobile bearing component 16 of the illustrated embodiments are distinguished primarily in the shapes of the components at the junctions of the stems 38, 40 and the distal or inferior surfaces 46, 48 of the bearings. First considering the fixed bearing component 14 of FIGS. 4 and 6-7, the bearing component has a pair of spaced curved protrusions or tabs 58, 60. The protrusions or tabs 58, 60 extend outward from the outer surface of the stem 38 and downward or distally from the distal or inferior surface 46 of the bearing. The protrusions or tabs 58, 60 include radial surfaces 62, 64 (see FIG. 4) lying in a plane that is perpendicular to the longitudinal axis 54 of the stem 38 and four stop surfaces 66, 68, 70, 72 (see FIG. 7) that are perpendicular to the radial surface 62, 64. As shown in FIG. 7, the protrusions or tabs 58, 60 are complementary in shape to the recesses 39, 41 in the tibial base component 12 so that when the fixed bearing 14 is assembled with the tibial base component 12, the radial surfaces 62, 64 of the bearing are supported on the radial surfaces 43, 45 of the base component and the bearing stop surfaces 66, 68, 70, 72 bear against the stop surfaces 47, 49, 51, 53 of the base component. The maximum transverse dimension of the stem 38 is at the protrusions or tabs 58, 60, and the maximum transverse dimension of the longitudinal bore 36 is at the recesses 39, 41; within the same transverse plane, the transverse dimensions of the stem 38 and longitudinal bore 36 are less at the spaces between the protrusions and between the recesses. Thus, the protrusions or tabs 58, 60 and recesses 39, 41 define mating keys and keyways. When the fixed bearing 14 is assembled with the tibial base 12, the protrusions 58, 60 and recesses 39, 41 define mating anti-rotation features that fix the rotational position of the bearing 14 with respect to the tibial base component 12.

It will be appreciated that the anti-rotation features of the fixed bearing component and tibial base component may have configurations different from those illustrated. Generally, the longitudinal bore 36 of the base component 12 is non-circular in transverse cross-section along a portion of its axial length and the stem 38 of the fixed bearing component 14 is non-circular in transverse cross-section along at least a portion of its length (see FIG. 7). These non-circular portions are located at the same axial position so that they may interact to limit or prevent relative rotation about the axes 32, 54 of the complementary stems 38, 26. Depending on the thickness of the tray portion 24 of the base component 12, the anti-rotation features could be positioned between the proximal or superior surface 28 of the tray and the distal or inferior surface 30 of the tray. Generally, however, the anti-rotation features would not extend beyond the proximal or superior surface 28 of the tray so that they do not interfere with use of the base component 12 with a mobile bearing such as mobile bearing 16.

A substantial part of the longitudinal bore 36 of the base stem 26 is circular in transverse cross-section (see FIGS. 8 and 12), so that the same base component 12 can be used with the mobile bearing component 16. The stem 40 of the mobile bearing component is circular in transverse cross-section along its entire axial length; there is no portion of the stem that is non-circular in transverse cross-section. The maximum outer diameter of the stem 40 of the mobile bearing component is less than the distance between inner edges of the radial surfaces 43, 45 of the base component 12; accordingly, no part of the mobile bearing component 16 is received in the recesses 39, 41 of the tibial base component 12. Thus, the mobile bearing component 16 is free to rotate about the central longitudinal axis 56 of the stem 40 when assembled with the tibial base component 12.

The fixed and mobile bearing components 14, 16 may be made of standard bearing materials. For example, a polymer such as ultrahigh molecular weight polyethylene may be used. If ultrahigh molecular weight polyethylene is used, it may be desirable to use a cross-linked form of this material. Use of such a polymer should be advantageous in that the protrusions or tabs of the fixed bearing 14 may be flexible for rigid assembly of the fixed bearing 14 and the tibial base 12.

It will be appreciated that a prosthetic knee system utilizing the features of the present invention would include several sizes of each of the components 10, 12, 14, 16. Generally, the size and shape of the stem of each size of tibial base component 12 and the sizes and shapes of the stems of each size of bearing component 14, 16 will preferably be the same throughout the system so that bearing components having different sizes or shapes of bearing surfaces can be used with different sizes of base components 12. Different sizes or shapes of tibial inserts may be used interchangeably on a single size of tibial base component. For example, two different sizes of fixed bearing tibial inserts could be used on a single size of tibial base component and two different sizes of mobile bearing inserts could be used on a single size of tibial base component. Thus, the bearing component that provides the optimum contact surface for the femoral component can be selected for both fixed and mobile bearings. Concerns associated with reduced contact areas, edge loading, contact stress and polyethylene wear from mismatched femoral components and fixed tibial bearings should be reduced or eliminated.

In addition, with a common or integrated tibial base component used for both fixed and mobile bearing applications, inventories should be substantially reduced, reducing inventory costs. Economies of scale with a common or integrated tibial base component should also reduce manufacturing costs. With the common or integrated tibial base component having a highly polished proximal or superior surface 28, backside wear of both the fixed and mobile bearing components 14, 16 should be reduced.

The components of the prosthetic knee system of the present invention may have other features common in the industry, and the prosthetic knee system could include additional components. For example, femoral and tibial augments could be included in the system and the femoral component 10 and tibial base component 12 could include features that allow for fixation of augments to the components 10, 12. Metaphyseal sleeves and stem extensions could also be included in the system. With a common or integrated tibial base component, a common group of augments, sleeves and stems can be used. The femoral and tibial base components 10, 12 may be porous, for bone ingrowth, or may include recesses for cemented fixation. The tibial base component may have keels on the distal side. The bearing surfaces of the bearing components may vary from that illustrated. Overall, features included as parts of existing prosthetic knee systems (primary and revision), such as the P.F.C.® Sigma™ knee system, the LCS® Complete™ knee system, the S-ROM® Noiles™ Rotating Hinge knee system and LPS (Limb Preservation System) system of DePuy Orthopaedics, Inc. of Warsaw, Ind., and competitive systems, may be incorporated into the prosthetic knee system of the present invention.

In use, the orthopaedic surgeon may use standard instruments and procedures to prepare the distal femur and proximal tibia to receive the femoral component 10 and tibial base component 12. Only a single set of instruments are needed for implanting the common or integrated tibial base component 12.

The surgeon has the option of selecting either the fixed bearing component 14 or the mobile bearing component 16. If the fixed bearing component 14 is selected, the surgeon may select the most appropriate size for the femoral component that has been selected. If the mobile bearing component 16 is selected, the surgeon may evaluate intraoperatively whether the mobile bearing is suitable for the particular patient: if the surgeon observes uncorrectable bearing spinout or undesirable joint balance, the surgeon may easily switch to a fixed bearing to suit the particular patient.

Post-operatively, if the patient experiences bearing spinout or joint instability, or if the surgeon determines that it is appropriate to revise the knee, the tibial base component 12 need not be removed if it is not loose. Instead, the surgeon could revise the mobile bearing knee to a fixed bearing knee without removing the tibial base component; the mobile bearing component 16 can be replaced with a fixed bearing component 14 without changing the base component 12. Similarly, if the surgeon determines that an originally-implanted fixed bearing tibial insert has worn unduly, the surgeon may replace the fixed bearing tibial insert with a mobile bearing tibial insert during revision surgery without changing the tibial base component.

It should be understood that the tibial base component and tibial inserts could be designed to provide an offset stem. In addition, although in the illustrated embodiments the tibial bases and tibial inserts both include elongate stems, the trays and inserts could include bosses or protuberances of shorter lengths instead of elongate stems. For example, the trays and inserts, or the inserts alone, could end distally at the transverse plane extending through the radial surfaces 43, 45, 62, 64.

Figure 9:
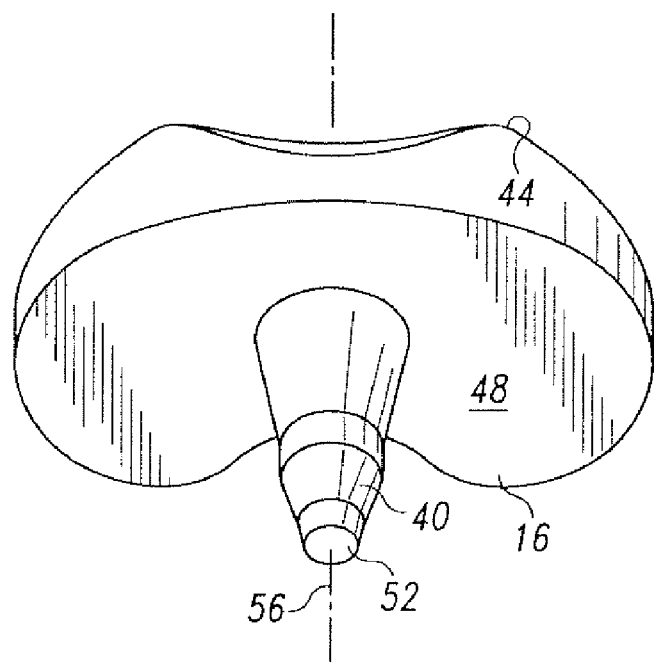
FIG. 9 is a perspective view of the other tibial bearing components of the system of the present invention.
Figure 14:
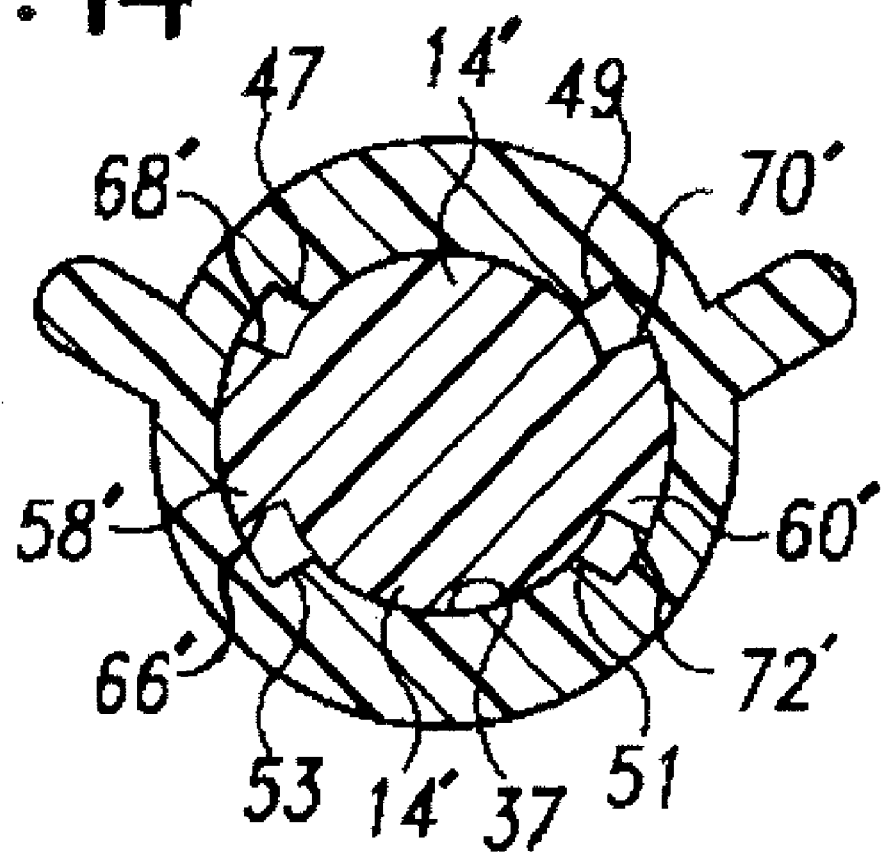
FIG. 14 is a cross-section similar to FIGS. 7 and 11 illustrating an alternative tibial bearing component that allows for limited rotation.

Moreover, the tibial bearing component could include protrusions or tabs similar to those illustrated at 58, 60 but having a shorter arc length that the recesses 39, 41 in the tibial base. Such a tibial bearing insert is illustrated in FIG. 14, and would allow for limited rotation. As illustrated the tibial insert 14' includes two protrusions or tabs 58', 60' with four stop surfaces 66', 68', 70', 72' that are perpendicular to the radial surfaces of the tabs 58', 60'. Such a tibial insert could be provided as an alternative to the mobile insert of FIGS. 9-11, or could be provided as a third alternative insert.

While only specific embodiments of the invention have been described and shown, it is apparent that various alternatives and modifications can be made thereto. Moreover, those skilled in the art will also recognize that certain additions can be made to these embodiments.

Examples of modifications and additions that may be made to the illustrated embodiments may be found in the following United States Provisional Patent Applications, the complete disclosures of which are incorporated by reference herein: U.S. Provisional Patent Application Ser. No. 60/829,430, entitled "MOBILE/FIXED PROSTHETIC KNEE SYSTEM," filed on Oct. 13, 2006 by Stephen A. Hazebrouck, Joel T. Outten and Gary To; and U.S. Provisional Patent Application Ser. No. 60/829,432, entitled "MOBILE/FIXED PROSTHETIC KNEE SYSTEMS," filed on Oct. 13, 2006 by Luke J. Aram, Adam I. Hayden, Stephen A. Hazebrouck, Anthony D. Zannis, Gary D. Barnett, Thomas S. Camino, Daniel D. Auger, Joseph G. Wyss, John A. Bonitati and Scott E. Dutiel.

It is the intention in the appended claims to cover all such alternatives, modifications and additions as may fall within the true scope of the invention.

We claim:

1. A prosthetic knee system comprising:
a femoral component having bearing surfaces;
a tibial base component comprising a tray having a flat proximal surface, a distal surface and an interior surface defining a bore having a central longitudinal axis, the bore being circular in transverse cross-section along a portion of the length of the bore, a portion of the interior surface of the bore having interior stop surfaces and interior radial surfaces, the interior stop surfaces being perpendicular to the interior radial surfaces and the interior radial surfaces being perpendicular to the longitudinal axis of the bore, the interior stop surfaces and interior radial surfaces defining spaced radial recesses, each radial recess having an arc length;
a first tibial bearing component having a proximal bearing surface, a flat distal surface and a protuberance extending distally from the flat distal surface, the protuberance having a longitudinal axis and a distal end spaced from the flat distal surface; and
a second tibial bearing component having a proximal bearing surface, a distal surface and a protuberance extending distally from the flat distal surface, the protuberance having a longitudinal axis and a distal end spaced from the distal surface;
wherein the first tibial bearing component is sized and shaped so as to be capable of being selectively assembled with the tibial base component with at least a portion of the protuberance received in the bore and the second tibial bearing component is sized and shaped so as to be capable of being selectively assembled with the tibial base component with at least a portion of the protuberance received in the bore;
wherein the first tibial bearing component includes a plurality of spaced tabs extending radially outward from the protuberance, each tab including a radial surface perpendicular to the longitudinal axis of the protuberance and a pair of stop surfaces perpendicular to the radial surface of the protuberance, each tab having an arc length;
wherein the tabs of the first tibial bearing component are receivable within the radial recesses of the tibial base component, the arc length of each tab being less than the arc length of each radial recess to allow for limited rotation of the first tibial bearing component on the tibial base component;
wherein the second tibial bearing component is shaped so as to be rotatable about the longitudinal axis of the stem when assembled with the tibial base component; and
wherein no part of the second tibial bearing component is received within the radial recesses of the tibial base component when the second tibial bearing component is assembled with the tibial base component.

2. The prosthetic knee system of claim 1 wherein the tibial base component includes a stem and wherein the bore extends into the stem.

3. The prosthetic knee system of claim 2 wherein the protuberance of the first tibial bearing component comprises a stem and the protuberance of the second tibial bearing component comprises a stem.

4. A prosthetic knee system comprising:
a femoral component having bearing surfaces;
a tibial base component comprising a tray and a stem, the tray having a flat proximal surface and a distal surface, the stem extending distally from the distal surface of the tray, the stem having a longitudinal axis and a distal end spaced from the tray;
the tibial base component having an interior surface extending distally from the proximal surface of the tray and defining a longitudinal bore contained within the stem, the longitudinal bore extending from the stem through the tray and through the proximal surface of the tray, wherein the longitudinal bore is circular in transverse cross-section along a portion of the axial length of the longitudinal bore within the stem;
the interior surface of the tibial base component including interior stop surfaces and radial interior surfaces perpendicular to the longitudinal axis of the stem, the interior stop surfaces and radial interior surfaces defining spaced radial recesses, the stop surfaces being at the ends of the radial recesses, the radial recesses being positioned opposite to each other and defining undercuts, the radial interior surfaces being distal to the distal surface of the tray;
a first tibial bearing component having a proximal bearing surface, a flat distal surface and a stem extending distally from the flat distal surface, the stem of the first tibial bearing component having a longitudinal axis and a distal end spaced from the flat distal surface, the proximal bearing surface and the stem of the first tibial bearing component comprising an integral unitary structure, the first tibial bearing component having a plurality of spaced radial protrusions extending radially outward from the stem of the first tibial bearing component, each protrusion including a surface perpendicular to the longitudinal axis of the stem of the first tibial bearing component and a pair of stop surfaces, the spaced radial protrusions being positioned opposite to each other and spaced from the flat distal surface of the first tibial bearing component; and a second tibial bearing component having a proximal bearing surface, a distal surface and a stem extending distally from the flat distal surface, the stem of the second tibial bearing component having a longitudinal axis and a distal end spaced from the distal surface, the stem of the second tibial bearing component being circular in transverse cross-section along its entire length;

wherein the first tibial bearing component is sized and shaped so as to be capable of being selectively assembled with the tibial base component with at least a portion of the stem of the first tibial bearing component received in the longitudinal bore and the second tibial bearing component is sized and shaped so as to be capable of being selectively assembled with the tibial base component with at least a portion of the stem of the second tibial bearing component received in the longitudinal bore; and wherein the protrusions of the first tibial bearing component are sized and shaped to be received in the radial recesses of the tibial base component to fix the rotational position of the first tibial bearing component with respect to the tibial base component when assembled and wherein the second tibial bearing component is shaped so that no part of the second tibial bearing component is received within the radial recesses of the tibial base component so that the second tibial bearing component is rotatable about the longitudinal axis of the stem of the second tibial bearing component when assembled with the tibial base component.

5. A prosthetic knee system comprising:

a femoral component having bearing surfaces;

a tibial base component comprising a tray and a stem, the tray having a planar proximal surface and a distal surface, the stem extending distally from the distal surface of the tray, the stem having a longitudinal axis, a distal end spaced from the tray and an interior surface defining a longitudinal bore contained within the stem;

the interior surface extending distally from the proximal surface of the tray into the stem;

the longitudinal bore extending from the stem through the tray and through the proximal surface of the tray;

wherein the interior surface includes a plurality of interior stop surfaces and a plurality of surfaces perpendicular to the longitudinal axis of the stem, the interior stop surfaces and perpendicular interior surfaces defining spaced radial recesses, the stop surfaces being at the ends of the radial recesses, each radial recess having an arc length;

a first tibial bearing component having a proximal bearing surface, a flat distal surface and a stem extending distally from the flat distal surface, the stem having a longitudinal axis and a distal end spaced from the flat distal surface, the first tibial bearing component having a plurality of spaced protrusions extending radial outward from the stem at the juncture of the stem and the distal surface of the first tibial bearing component, each protrusion including a radial surface perpendicular to the longitudinal axis of the stem and a pair of stop surfaces perpendicular to the radial surface, each radial protrusion having an arc length between the stop surfaces; and a second tibial bearing component having a proximal bearing surface, a distal surface and a stem extending distally from the flat distal surface, the stem having a longitudinal axis and a distal end spaced from the distal surface, wherein the stem of the second tibial bearing component is circular in transverse cross-section along the entire axial length of the stem;

a third tibial bearing component having a proximal bearing surface, a flat distal surface and a stem extending distally from the flat distal surface, the stem having a longitudinal axis and a distal end spaced from the flat distal surface, the third tibial bearing component having a plurality of spaced protrusions extending radially outward from the stem at the juncture of the stem and the distal surface of the third tibial bearing component, each protrusion including a radial surface perpendicular to the longitudinal axis of the stem and a pair of stop surfaces perpendicular to the radial surface, each radial protrusion having an arc length between the stop surfaces; and wherein the first tibial bearing component, second tibial bearing component and third tibial bearing component are each sized and shaped so as to be capable of being selectively assembled with the tibial base component with at least a portion of the stem of the selected tibial bearing component received in the longitudinal bore of the tibial base component;

wherein the arc lengths of the radial protrusions of the first tibial bearing component are substantially the same as the arc lengths of the radial recesses of the tibial base component to fix the rotational position of the first tibial bearing component with respect to the tibial base component when the stem of the first tibial bearing component is received in the longitudinal bore of the tibial base component; and wherein the longitudinal bore of the tibial base component and the stem of the second tibial bearing component are sized and shaped so that the second tibial bearing component can rotate about the longitudinal axis of the stem when the stem of the second tibial bearing component is received in the longitudinal bore of the stem of the tibial base component; and wherein no part of the second tibial bearing component is received within the radial recesses when the second tibial bearing component is assembled with the tibial base component; and wherein the arc lengths of the radial protrusions of the third tibial bearing component are less than the arc lengths of the radial protrusions of the first tibial bearing component and less than the arc lengths of the radial recesses of the tibial base component to allow limited rotation of the third tibial bearing component with respect to the tibial base component when the stem of the third tibial bearing component is received in the longitudinal bore of the tibial base component.

6. A prosthetic knee system comprising:

a femoral component having bearing surfaces;

a tibial base component comprising a tray having a flat proximal surface, a distal surface and an interior surface defining a bore, the bore being circular in transverse cross-section along a portion of the length of the bore, a portion of the interior surface of the bore having interior stop surfaces and a portion of the interior surface of the bore being radial surfaces perpendicular to the stop surfaces and perpendicular to the longitudinal axis of the bore, the interior stop surfaces and radial surfaces defining spaced radial recesses, each radial recess having an arc length;

a first tibial bearing component having a proximal bearing surface, a flat distal surface and a protuberance extending distally from the flat distal surface, the protuberance having a longitudinal axis and a distal end spaced from the flat distal surface; and a second tibial bearing component having a proximal bearing surface, a flat distal surface and a protuberance extending distally from the flat distal surface, the protuberance having a longitudinal axis and a distal end spaced from the distal surface;

a third tibial bearing component having a proximal bearing surface, a flat distal surface and a protuberance extending distally from the flat distal surface, the protuberance having a longitudinal axis and a distal end spaced from the distal surface;

wherein the protuberances of all three tibial bearing components have the same size and shape;

wherein the protuberances of all three tibial bearing components are sized and shaped so as to be capable of being selectively assembled with the tibial base component with at least a portion of the protuberance received in the bore of the tibial base component;

wherein the first tibial bearing component includes a plurality of spaced tabs extending radially outward from the protuberance, each tab including a radial surface perpendicular to the longitudinal axis of the protuberance and a pair of stop surfaces perpendicular to the radial surface of the protuberance, each tab having an arc length substantially the same as the arc lengths of the radial recesses of the tibial base component so that when the first tibial bearing component is assembled with the tibial base, the tabs of the first tibial bearing component are received within the radial recesses of the tibial base component to prevent relative rotation between the first tibial bearing component and the tibial base;

wherein the second tibial bearing component includes a plurality of spaced tabs extending radially outward from the protuberance, each tab including a radial surface perpendicular to the longitudinal axis of the protuberance and a pair of stop surfaces perpendicular to the radial surface of the protuberance, each tab having an arc length less than the arc lengths of the radial recesses of the tibial base component so that when the second tibial bearing component is assembled with the tibial base, the tabs of the second tibial bearing component are received within the radial recesses of the tibial base component to allow for limited relative rotation between the second tibial bearing component and the tibial base; and wherein no part of the third tibial bearing component is received within the radial recesses of the tibial base component when the third tibial bearing component is assembled with the tibial base component.

* * * * *